United States Patent [19]

Wagner et al.

[11] 4,028,306
[45] June 7, 1977

[54] UREA OR CARBONAMIDE CONTAINING DIISOCYANATE POLYADDITION PRODUCTS WITH PHOSPHORIC ESTER SUBSTITUENTS

[75] Inventors: Kuno Wagner, Leverkusen-Steinbuechel; Manfred Hajek, Cologne, both of Germany

[73] Assignee: Bayer Aktiengesellschaft, Leverkusen, Germany

[22] Filed: June 2, 1975

[21] Appl. No.: 583,133

[30] Foreign Application Priority Data

June 5, 1974 Germany ................... 2427090

[52] U.S. Cl. .................. 260/75 NT; 260/77.5 AT
[51] Int. Cl.² ................................ C08G 18/73
[58] Field of Search ............... 260/77.5 AT, 75 NT

[56] References Cited

UNITED STATES PATENTS

| | | | |
|---|---|---|---|
| 2,691,567 | 10/1954 | Kvalnes et al. | 260/77.5 AT X |
| 3,277,212 | 10/1966 | Fischer et al. | 260/77.5 AT X |
| 3,334,056 | 8/1967 | Fischer et al. | 260/77.5 AT X |
| 3,456,040 | 7/1969 | Onodera et al. | 260/77.5 AT X |
| 3,470,271 | 9/1969 | Brotherton et al. | 260/77.5 AT X |
| 3,551,527 | 12/1970 | Weber et al. | 260/77.5 AT X |

*Primary Examiner*—Sandra M. Person
*Attorney, Agent, or Firm*—Gene Harsh; Lawrence S. Pope; Frederick H. Colen

[57] ABSTRACT

The present invention relates to linear, film-forming diisocyanate polyaddition products soluble in lacquer solvents which contain 10 to 69 wt. % of structural units of the formula:

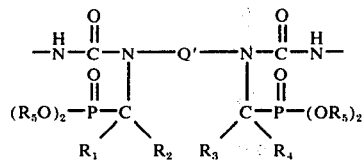

and processes for producing such diisocyanate polyaddition products. The polymer produced may be polyureas, polyhydrazocarbonamide, a polyurethane polyurea, polyurethane polyhydrazocarbonamides, polyurea polyhydrazocarbonamides or polyurethane polyurea polyhydrazocarbonamides. These diisocyanate polyaddition products are useful for the production of surface coatings, lacquer coatings and impregnations.

23 Claims, No Drawings

UREA OR CARBONAMIDE CONTAINING DIISOCYANATE POLYADDITION PRODUCTS WITH PHOSPHORIC ESTER SUBSTITUENTS

FIELD OF THE INVENTION

This invention relates to new high molecular weight diisocyanate polyaddition products containing phosphonic acid ester groups as lateral substituents on urea segments in their molecular structure. The new diisocyanate polyaddition products, which may vary from elastic to hard, are distinguished by outstanding film-forming properties, improved gloss, improved fireproof properties and reduced viscosity of solutions thereof. The invention also relates to a new process for producing these linear, thermoplastic diisocyanate polyaddition products with an extremely high urea group content, and to the use of diisocyanate polyaddition products for the production of surface coatings, lacquer coatings and impregnations.

BACKGROUND OF THE INVENTION

There are already numerous processes for producing high molecular weight crosslinked and uncrosslinked diisocyanate polyaddition products of average and high molecular weight which are soluble in organic solvents. In these processes, water, glycols, diamines, hydrazines, hydrazine hydrate, hydrazine derivatives or carbodihydrazide, for example, are used as chain extenders and crosslinkers (German Auslegeschrift Nos. 1048408, 1183196 and 1184984, German Offenlegungsschrift No. 2015603 or U.S. Pat. Nos. 3248424, 3184426 or 3399167).

In conventional isocyanate polyaddition processes, it is often difficult to synthesize high molecular weight polyaddition compounds with a high content of urethane and, more especially, urea or hydrazodicarbonamide groups because, on account of their isocyanate-reactive hydrogen atoms, these groups actually lead, during the polyaddition reaction, to undesirable branching especially in the production of solutions with high solids content. However, since solubility and thermoplastic processibility of the polyaddition compounds are governed to a considerable extent by the linear structure of the macromolecule, the production of soluble, thermoplastically processible isocyanate polyaddition products has hitherto been confined to relatively narrow ranges of urethane and, more especially, urea or hydrazodicarbonamide contents. For example, experience has shown that the production, from difunctional NCO-prepolymers and water or diamines as chain extenders, of soluble polyurethane polyureas, which are storable in solution form and do not show any tendency towards gelation, is particularly difficult when the content of chain-extending urea groups —NH—CO—NH— exceeds a level of 5.2% by weight. In this case, and especially when the NCO-prepolymer are chain-extended in an NCO:NH₂ ratio of 0.9 to 1.2, it is only possible to obtain readily gelling solutions of limited shelf life in which from 10 to 20% by weight of gel fractions may be detected by centifuging. These gel fractions are insoluble, for example, even in strongly polar solvents, such as dimethylformamide or dimethylacetamide, and may only be dissolved over prolonged periods at elevated temperatures, accompanied by the heat-induced breakup of crosslink sites. If the concentration of the

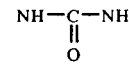

units in the solid product is increased to between 8 and 10% by weight or more, completely insoluble polyaddition products are obtained because, on the one hand, the urea groups are able to react to form biuret branchings and crosslinks and because, on the other hand, the concentrations of urea segments capable of forming strong hydrogen bridge bonds is so high that reversible gels begin to form at room temperature. The products in question are branched polyaddition products which only dissolve under the action of heat, generally at temperatures in the range of from 50° to 70° C. Even when optimum manufacturing techniques are applied, for example, gradual introduction of the NCO-prepolymers at low temperatures into dilute solutions of the chain extenders, apparently stable solutions often gel after only a short time. Their dispersion or dissolution involves considerable difficulties so that it is not possible to produce, for example, elastomeric lacquer coatings, sheet structures and coatings on wood, metal, fabric or leather substrates, plastics-based lacquer finishes and coatings. High urea group concentrations in the polyaddition products coupled with high solids contents of, for example, from about 30 to 50% and with high molecular weights (NCO-NH₂ ratio = 1) have in the past always resulted in the formation of reversibly gelling or crosslinked, irreversible gels, even where dimethylformamide is used as solvent.

It has now surprisingly been found that extremely high molecular weight, readily soluble, linear and, hence, also thermoplastically processible or film forming (from solutions of high solids concentration), polyurethane ureas, polyureas, polyurethane-polyurea-polyhydrazodicarbonamides or polyurethane-polyhydrazodicarbonamides with optionally very high urea and/or hydrazodicarbonamide concentrations, may be obtained in a smooth, reproducible reaction providing the urea segments of the polyaddition products are partially or completely substituted by organic phosphonic acid ester radicals.

SUMMARY OF THE INVENTION

Accordingly, the present invention relates to linear, film-forming diisocyanate polyaddition products soluble in lacquer solvents, characterized by the fact that they contain from about 10 to 69% by weight of structural units of the formula:

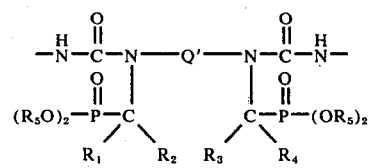

wherein

Q' represents preferably a hydrocarbon radical such as a divalent $C_2$–$C_{18}$ alkyl radical, $C_4$–$C_{13}$ cycloalkyl radical, $C_7$–$C_{11}$ aralkyl radical or $C_6$–$C_{14}$ aryl radical optionally interrupted by oxygen, sulphur or nitrogen and optionally substituted by a $C_1$–$C_8$ alkyl radical, $N(R_6)_2$, [$R_6 = C_1$–$C_8$ alkyl radical, $C_4$–$C_{10}$ cycloalkyl radical, $C_7$–$C_{11}$ aralkyl radical], $NO_2$— and/or halogen atoms, $R_1$ and $R_2$ are the same or different and represent hydrogen or a $C_1$–$C_{18}$ alkyl radical, $C_4$–$C_{10}$ cycloalkyl radical or a $C_6$–$C_{10}$ aryl radical, $R_3$ and $R_4$ are the same or different and represent hydrogen, a $C_1$–$C_{18}$ alkyl radical, $C_4$–$C_{10}$ cycloalkyl radical, $C_6$–$C_{10}$ aryl radical, in addition to which $R_1$ and $R_2$ or $R_3$ and $R_4$ together with the carbon atoms between nitrogen and phosphorus can form a 5 to 7 membered isocyclic ring, and $R_5$ represents a $C_1$–$C_4$ alkyl, cyclohexyl or phenyl radical.

The invention also relates to a process for producing these diisocyanate polyaddition products by reacting diisocyanate with relatively high molecular weight compounds containing two terminal hydroxyl groups and/or amino groups and having molecular weights in the range of from about 400 to 8000, and optionally water and/or diols with a molecular weight below 400 and/or diamines with a molecular weight below about 400 and/or hydrazines with a molecular weight below about 400 as chain extending agents, which is characterized by the fact that diamines corresponding to the formula:

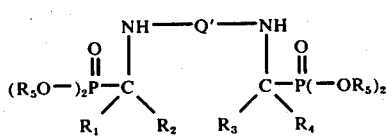

are used in the polyaddition reaction in such quantities that the addition products contain from about 10 to 69% by weight of structural units corresponding to the formula:

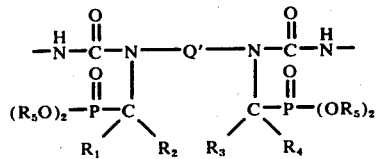

wherein $R_1$, $R_2$, $R_3$, $R_4$, $R_5$ and $Q'$ are as defined above.

Finally, the invention also relates to the use of these diisocyanate polyaddition products for the production of surface coatings, lacquer coatings and impregnations.

DETAILED DESCRIPTION OF THE INVENTION

It is essential for the process according to the invention to use chain-extending agents (A) corresponding to the formula:

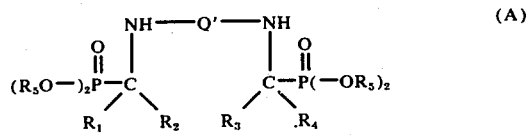

in the isocyanate polyaddition reaction known per se. In the process according to the invention, in addition to the diamines containing phosphonic acid ester groups which are essential to the invention, it is also possible to use any known, preferably defunctional, starting materials for the production of diisocyanate polyaddition products. By using the essential diamines in accordance with the invention, it is possible to produce linear diisocyanate polyaddition products containing groups of the formula:

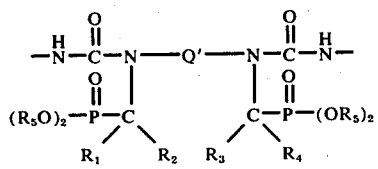

in a proportion of about 10 to 69% by weight, preferably in a proportion of about 15 to 25% by weight, such substantially corresponds to a urea segment (=N—CO—N=) content of from about 3.6 to 17% by weight, preferably from about 4 to 14% by weight.

In one embodiment of the process according to the invention, the chain-extending agents (A) essential to the invention are used as such. In another embodiment, the chain-extending agents essential to the invention are converted by reaction with at least 2 mols of a diisocyanate, $Q(NCO)_2$, per mol of chain-extending agent (A) into the corresponding NCO-prepolymers (B) corresponding to the formula:

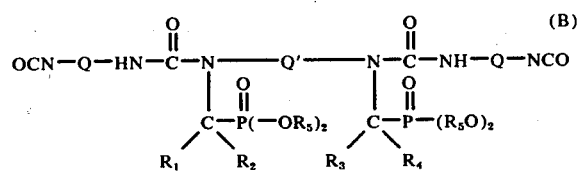

which in turn may be used as isocyanate component in the process according to the invention. It is, of course, also possible to use both chain-extending agent (A) and also NCO-prepolymer (B) simultaneously in the process according to the invention. In the process according to the invention, the quantities in which components (A) and (B) according to the invention are used are always selected in such a way that the end products of the process according to the invention contain from 10 to 69% by weight and preferably from 15 to 25% by weight of structural units corresponding to the formula:

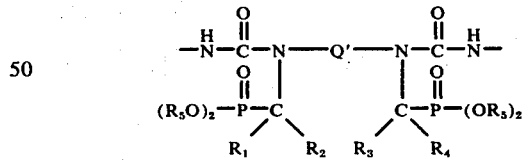

In formulae (A) and (B) above and also in the following; the radicals $R_1$ – $R_5$, Q and $Q'$ having the following meanings:

$R_1$, $R_2$, $R_3$ and $R_4$ are the same or different and represent hydrogen, a $C_1$–$C_{18}$ alkyl radical, $C_4$–$C_{10}$ cycloalkyl radical, $C_6$–$C_{10}$ aryl radical, in addition to which $R_1$ and $R_2$ or $R_3$ and $R_4$, together with the carbon atom between the nitrogen and phosphorus, may form a 5— to 7— membered isocyclic ring;

$R_1$, $R_2$, $R_3$, and $R_4$ and preferably represent hydrogen, an aliphatic hydrocarbon radical with 1 to 4 carbon atoms or an aromatic hydrocarbon radical with 6 to 10 carbon atoms. Compounds of formulae (A) and (B), in which $R_1$ and $R_2$ or $R_3$ and $R_4$ together with the carbon atom between nitrogn and phosphorus, can form a 5— to 7-isocyclic ring, are also preferred.

$R_5$ represents a $C_1$–$C_4$ alkyl radical, a cyclohexyl radical or even a phenyl radical. $R_5$ preferably represents an aliphatic $C_1$–$C_4$ hydrocarbon radical.

Q' represents preferably a hydrocarbon radical such as a divalent $C_2$–$C_{18}$ alkyl radical, $C_4$–$C_{13}$ cycloalkyl radical, $C_7$–$C_{11}$ aralkyl radical or $C_6$–$C_{14}$ aryl radical optionally interrupted by oxygen, sulphur or nitrogen and optionally substituted by a $C_1$–$C_8$ alkyl radical, $N(R_6)$ [$R_6 = C_1$–$C_8$ alkyl radical, $C_4$–$C_{10}$ cycloalkyl radical, $C_7$–$C_{11}$ aralkyl radical], nitro and/or halogen atoms. Q' preferably represents an aliphatic $C_2$–$C_8$ hydrocarbon radical, a cycloaliphatic $C_6$–$C_{13}$ hydrocarbon radical, an araliphatic $C_7$–$C_8$ hydrocarbon radical or an aromatic $C_6$–$C_{14}$ hydrocarbon radical.

Q quite generally represents the radical obtained by removing the isocyanate groups from an organic diisocyanate with a molecular weight in the range of from 140 to 6000. Q preferably represents an aliphatic $C_4$–$C_{12}$ hydrocarbon radical, a cycloaliphatic $C_4$–$C_{15}$ hydrocarbon radical, an aromatic $C_6$–C-hydrocarbon radical or an araliphatic $C_7$–$C_8$ hydrocarbon radical.

It is always preferred to use the formula (B) urea diisocyanates containing phosphonic acid ester groups and $\alpha,\omega$-NCO-groups, employed in accordance with the invention, in cases where solvent mixtures containing alcohol are used as solvents for carrying out the polyaddition reaction, for example solvent mixtures of toluene or xylene and isopropanol, tert.-butanol etc. In contrast, the bifunctional aminophosphonic acid esters of formula (A) may be used equally successfully in alcohol-free or anhydrous solvents, such as dimethylformamide or dimethylformamide/xylene, dimethylformamide/methylethyl ketone mixtures, etc. in which case the absence of alcohols ensures that the chain-extending reaction takes place smoothly without premature chain termination by alcohols through the use of aminophosphonic acid esters of reduced basicity. In principle, the same end products of the process according to the invention may be obtained by using both compounds (A) and compounds (B) by suitably selecting the solvent.

The $\alpha$-aminoalkane phosphonic acid esters of formula (A) above used in accordance with the invention, although for the most part unreported and uncharacterized in the literature, may be obtained from bifunctional aldimines or ketimines and dialkylphosphites by addition reactions analogous to the conventional processes for producing monofunctional $\alpha$-aminoalkane phosphonic acid dialkyl esters in accordance with Houben-Weyl, Organische Phosphorverbindungen, Vol. XII/I, page 485 (1963). The preparation of compounds (A) and (B) essential to the invention is described by way of example in Examples 8a to 8f which relate to a few preferred representatives. Basically, compounds (A) are produced by the addition of phosphites of the formula $O=PH(R_5)_2$ to the $C=N$-double bond of bis-ketimines or bis-aldimines of the type obtainable by condensing diprimary diamines of the formula $Q'](NH_2)_2$ with aldehydes of ketones corresponding to the formula:

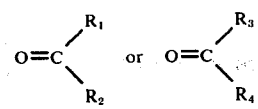

Carbonyl compounds preferably used for producing the aminophosphonic acid esters are formaldehyde, acetaldehyde, propionaldehyde, butyraldehyde, isobutyraldehyde, benzaldehyde, tolylaldehyde, cyclopentanone, cyclohexanone, methylethyl ketone, methylisopropyl ketone, methylisobutyl ketone. Unsaturated aldehydes, such as, acrolein, crotonaldehyde, or even cycloaliphatic aldehydes, such as cyclohexylaldehyde, are also suitable. It is particularly preferred to use isobutyraldehyde as the carbonyl compound.

Examples of diamines suitable for producing compounds (A) and (B) essential to the invention are ethylene diamine, 1,2-diaminopropane, 1,3-diaminopropane, propylene diamine, 1,4-diaminobutane, hexamethylene diamine, trimethyl hexamethylene diamine, diaminomethyl cyclobutane (by hydrogenating dimerized acrylonitrile), 3-amino-1-methylaminopropane, 3-aminodimethylaminopropane, 3,3'-diaminodipropylamine, methyl-bis-(3-aminopropyl)-amine, $\alpha,\omega$-diamino caproic acid methyl ester, hydrogenated thiodipropionic acid dinitrile, 3,3'-diamino-dipropyl ether, of the type which may be obtained from oligomeric polymerization of polyaddition products of propylene oxide (ethylene oxide) by reaction with ammonia under pressure in the presence of nickel as catalyst, perhydrogenated p-phenylene diamine, perhydrogenated 4, diaminodiphenylmethane, the perhydrogenated diamines of 4,4'-diaminodiphenyl ether and 4,4'-diaminodiphenyl thioether, m and p-xylylene diamine, 1-amino-3,3,5-trimethyl-5-aminomethyl cyclohexane (= isophorone diamine), also aromatic diamines, such as 2,4-diamino toluene, 2,6diamino toluene, 1,3-bis-aminomethyl-4,6-dimethylbenzene, 2,4-diamino-3,5-diethyl toluene, 2,6-diamino-3,5-diethyl toluene, 2,4-diamino-1,3,5-triisopropylbenzene, 4,4'-diaminodiphenyl methane, 4,4'-diaminodiphenyl ether and thioether, m- and p-phenylene diamine, 1,4- and 1,5-naphthylene diamine, 3,3'-diamino-3,3'-dichlorodiphenylmethane, 4,4'-diamino-3,3'-dichlorodiphenyl ether, 4,4'-diaminodiphenyl dimethylmethane, diaminomethyl-perhydrodicyclopentadiene, polyamines containing urethane or urea groups of the type which may be obtained for example, by reacting p-nitrophenyl isocyanate with low molecular weight polyols, such as ethylene glycol, 1,4-butane diol, hexane diol, or diamines, such as hexamethylene diamine, followed by hydrogenation. Particularly preferred diamines are hexamethylene diamine, 4,4'-diamino-dicyclohexylmethane, 1-amino-3,3,5-trimethyl-5-aminomethyl cyclohexane, 4,4'-diaminodiphenylmethane, 2,4-diamino toluene and 2,6-diamino toluene.

Dialkylphosphites preferred for carrying out the addition to aldimines and ketimines are dimethylphosphite, diethylphosphite, di-n-propylphosphite, diisopropylphosphite, di-n-butylphosphite. However, dicyclohexylphosphite and diphenyl-phosphite for example, are just as suitable. It is particularly preferred to use diethylphosphite.

The following are mentioned as examples of bifunctional aminophosphonic acid esters (A) suitable for use in accordance with the invention:

1) 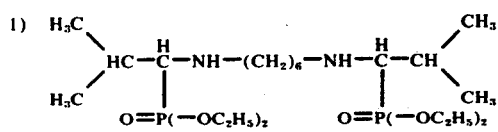
Molecular weight: 500

2) 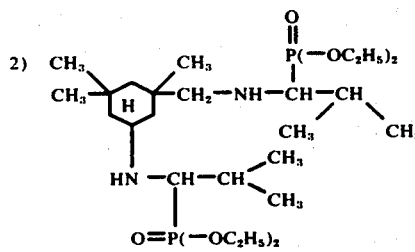
Molecular weight: 554

3) 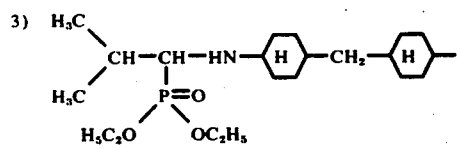
Molecular weight: 593

4) 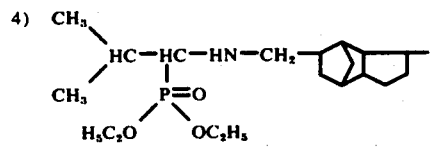
Molecular weight: 522

5) 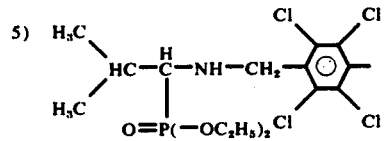
Molecular weight: 658

6) 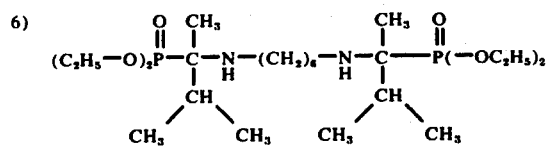
Molecular weight: 528

7) 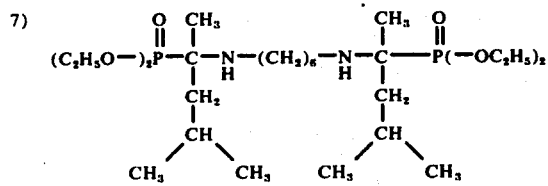

Molecular weight: 556

Preferred aminophosphonic acid esters are compounds (1), (2), (3), (6) and (7).

The preferred bifunctional α,ω-diisocyanato prepolymers of aminophosphonic acid esters (B) are the following:

1) 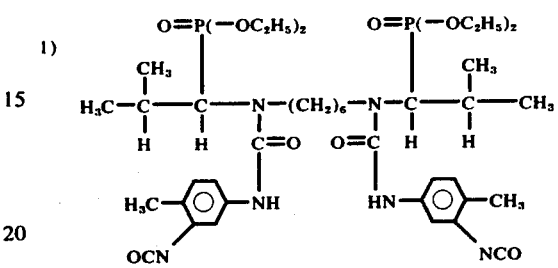
Molecular weight: 848

2) 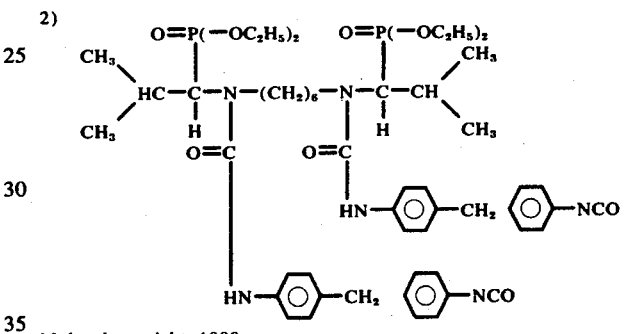
Molecular weight: 1000

3. The following compound is particularly preferred by virtue of its elasticizing properties:

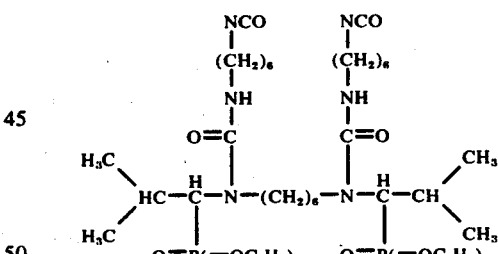
Molecular weight: 836

4) It is also preferred to use

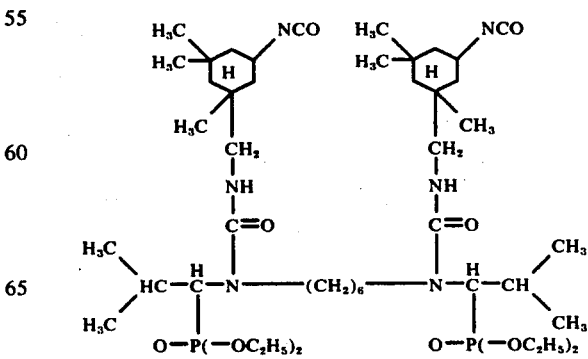

5)
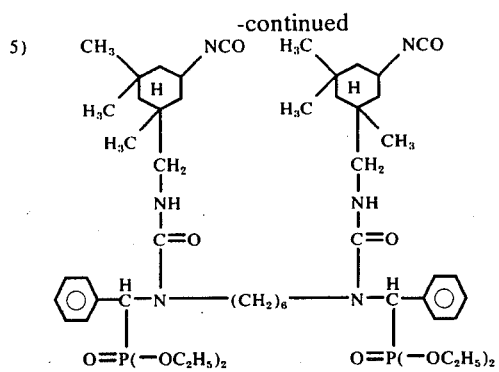

Molecular weight: 1012

These isocyanate-functional compounds (B) containing phosphonic ester groups are obtained by reacting at least 2 mols of monomeric diisocyanates Q(NCO)$_2$, with 1 mol of the bifunctional α-aminoalkyl phosphonic acid ester (A), preferably in 30 to 60% solution in an organic solvent, such as toluene, xylene, dimethylformamide (cf. also footnote to Example 1).

Aliphatic, cycloaliphatic, araliphatic or aromatic diisocyanates may be used as the diisocyanates, Q(NCO)$_2$, both for production of the compounds (B) to be used in accordance with the invention and also as reactants for the compounds (A) to be used in accordance with the invention in the diisocyanate polyaddition reaction known per se. Examples of these diisocyanates are 1,4-tetramethylene diisocyanate, 1,5-pentamethylene diisocyanate, 1,6-hexamethylene diisocyanate, 2,4,4-trimethyl hexamethylene-1,6-diisocyanate, 1,12-dodecamethylene diisocyanate, 1,2-diisocyanatomethyl cyclobutane, di-cyclohexyl-4,4'-diisocyanate, dicyclohexylmethane-4,4'-diisocyanate, p-and m-xylylene diisocyanate, lysine methyl ester diisocyanate, 1-isocyanato-3,3,5-trimethyl-5-isocyanatomethyl cyclohexane, 1-methyl-2,4-diisocyanato cyclohexane and isomers, 2,4-tolylene diioscyanate, 2,6-tolylene diisocyanate, 4,4'-diisocyanato-diphenylmethane, 4,4'-diisocyanato diphenyl ether, 1,5-naphthylene diisocyanate and NCO-telomers of the aforementioned diisocyanates of the type described in French Patent Specification No. 1,593,137, especially those of hexamethylene diisocyanate and 1-isocyanato-3,3,5-trimethyl-5-isocyanatomethyl cyclohexane with vinylacetate, vinyl chloride, styrene, acrylic acid methyl ester, methacrylic acid methyl ester and acrylic acid butyl ester. It is also possible to use diisocyanates containing semi-carbazide groups of the type mentioned in German Offenlegungsschrift No. 1,720,711 especially those of 2 mols of hexamethylene diisocyanate or 1-isocyanato-3,3,5-trimethyl-5-isocyanatomethyl cyclohexane and 1 mol of N,N-dimethylhydrazine. Preferred diisocyanates are hexamethylene diisocyanate, 1-isocyanato-3,3,5-trimethyl-5-isocyanatomethyl cyclohexane (≈ isophorone diisocyanate), dicyclohexylmethane-4,4'-diisocyanate, m- and p-xylylene diisocyanate, 2,4-toluene diisocyanate, 2,6-tolylene diisocyanate, 4,4'-diisocyanatodiphenylmethane 1,5-naphthylene diisocyanate and addition products of the aforementioned diisocyanates with α,ω-dihydroxyl polyesters or polyethers with molecular weights in the range of from 62 to 6000 in a molar ratio of 2:1.

The end products of the process according to the invention may be obtained from compounds (A) and (B) by the following methods and modified procedures known per se. Through comounds (A) and (B) it is possible to control product properties, solubility and viscosity properties, to improve fireproof properties and to avoid reversible or irreversible gel formation. The following modified procedures are adopted:

1. The direct polyaddition of relatively high molecular weight polyhydroxyl compounds, diisocyanates and α-aminophosphonic acid esters (A), optionally in the presence of known chain-extending agents with a molecular weight below 400, hereinafter referred to as (K), such as water, diols, such as ethylene glycol, diethylene glycol, triethylene glycol, 1,3-propane diol, 1,2-propane diol, 1,4-butane diol, thiodiglycol, 1,6-hexane diol, 1,8-octane diol, 1,12-dodecane diol, 1,4-dimethylolbenzene, hydrazine hydrate, hydrazine, N-methyl hydrazine, N,N-dimethyl and diethyl hydrazine, ethylene diamine, trimethylene diamine, 1,2-diaminopropylene diamine, tetramethylene diamine, N-methyl-1,3-propylene diamine, pentamethylene diamine, trimethyl hexamethylene diamine, hexamethylene diamine, octamethylene diamine, undecamethylene diamine, diaminomethyl cyclobutane, 1,4-diamino cyclohexane, 1,4-diaminodicyclohexyl methane, 1-methyl-2,4-diaminocyclohexane, 1-methyl-2,6-diaminocyclohexane, m-xylylene diamine, 1-amino-3,3,5-trimethyl-5-aminomethyl cyclohexane, p-aminobenzylamine, 3-chloro-4-aminobenzylamine, hexahydrobenzidine, 2,6-dichloro-1,4-diaminobenzene, p-phenylene diamine, tolylene-2,4-diamine, 1,3,5-triisopropyl-2,4-phenylene diamine, 1,3,5-trimethyl-2,4-phenylene diamine, 1-methyl-3,5-diethyl-2,4-phenylene diamine, 1-methyl-3,5-diethyl-2,4-phenylene diamine, 1-methyl-3,5-diethyl-2,6-phenylene diamine, 4,4'-diaminodiphenylmethane, 4,4-diaminodiphenyl ether, preferably hydrazine hydrate, N,N-dimethyl hydrazine, 1-amino-3,3,5-trimethyl-5-aminomethyl cyclohexane, hexamethylene diamine, m-xylylene diamine, 4,4-diaminodicyclohexyl methane, lysine methyl ester, trimethyl hexamethylene diamine, 1-methyl-2,4-diaminocyclohexane; from 1 to 20 mols, preferably from 1 to 3 mols of α-aminophosphonic esters may be used per mol of the relatively high molecular weight polyhydroxyl component, and polyaddition is preferably carried out in known manner in solvents free from hydroxyl groups, such as dimethylformamide, in an NCO/OH-NH$_2$-equivalent ratio of 0.95 to 1.2, preferably from 1 to 1.1.

2. Reacting a α,ω-diisocyanato prepolymers, i.e. α,ω-diisocyanato polyesters, polyethers and polythioethers and polyacetals, α,ω-diisocyanato polyurea polyethers, optionally in admixture with monomeric diisocyanates or NCO-prepolymers of formula (B), with the building components (A) optionally in the presence of the chain extenders (K).

3. Reacting with α,ω-diisocyanato prepolymers of the type defined in (2) and isocyanato functional compounds (B) containing phosphonic ester groups with the chain extenders (K).

4. Reacting relatively high molecular weight α,ω-diamino polyethers, α,ω-diamino polyurethanes, α,ω-diamino polyureas with the isocyanato functional compounds of formula (B), optionally in the presence of the chain extenders (K).

5. Reacting isocyanato functional compounds of formula (B) with diamines or hydrazines of the type defined in (1) above, in which case polyureas or polyhydrazodicarbonamides substituted by phosphonic ester groups are obtained.

6. Reacting monomeric diisocyanates Q(NCO)$_2$, with bifunctional aminophosphonic acid esters of the constitution (A).

In one preferred embodiment of the process according to the invention, prepolymers containing terminal isocyanate groups are initially prepared from the low molecular weight diisocyanates and the relatively high molecular weight dihydroxyl compounds in known manner by reacting the reagents in a NCO:OH ratio of 1.5 to 2.3, preferably from 1.8 to 2, and mixing the prepolymers thus obtained with the compounds (B) containing phosphonic ester groups. The reaction of these relatively high molecular weight mixtures containing terminal isocyanate groups with bifunctional aminophosphonic esters (A) and/or conventional chain extenders in accordance with the invention may be carried out either in substance or in solution at temperatures in the range of from −50° to +140° C, preferably at temperatures in the range of from 5° to 40° C. It may be of advantage to use the relatively high molecular weight diisocyanate if desired together with a 1 to 6-fold molar quantity of monomeric diisocyanates.

In the production of polyaddition products of extremely high molecular weight, it is preferred to use a molar ratio of (NCO-prepolymer + monomeric diisocyanate + (B)): (Chain extender) of 1:1.

Relatively high molecular weight dihydroxy compounds suitable for prepolymer formation and for use in the process according to the invention are, in particular, difunctional polyesters containing terminal hydroxyl groups and having a molecular weight in the range of from 400 to 8000, preferably from 800 to 2500, difunctional polyethers containing terminal hydroxyl groups and having a molecular weight in the range of from 400 to 8000, preferably from 800 to 2500, and corresponding difunctional dihydroxy polyacetals, dihydroxy polycarbonates, etc. Examples of these relatively high molecular weight dihydroxyl compounds widely known in polyurethane chemistry may be found, inter alia, in Kunststoff-Handbuch, Vol. VII, "Polyurethane", Carl-Hanser-Verlag Munich (1966), pages 47 to 74 and Polyurethanes: Chemistry and Technology, Part I Chemistry, Saunders and Frisch pages 32–61.

If desired, the catalysts commonly used in polyisocyanate chemistry, such as tertiary organic bases, alkali salts, metal salts, etc., may of course, be used for chain extension and for additionally accelerating the polyaddition reaction. Suitable catalysts are dimethylbenzylamine, N-methyl imidazole, triethylene diamine, tin-(II)octoate, tin(IV) dibutyl dilaurate, metal complexes of Co, Fe, Zn, Bi, Al, Cu, Ni, with acetal acetonates, acetoacetic esters, etc.

The process according to the invention is preferably carried out in the presence of organic solvents, such as dimethylformamide, acetone, methylethyl ketone, methylene chloride, chloroform, perchloroethylene, methylisopropyl ketone, benzene, toluene, xylene, ethyl acetate, butyl acetate, methylglycol, acetate, ethylglycol acetate, tetrahydrofuran or in the presence of solvent mixtures.

In cases where known diamines and hydrazines are used as chain extenders for isocyanato functional compounds containing phosphonic ester groups of type (B), it is also possible to use solvent mixtures containing alcohols, such as isopropanol, butanol, tert.-butanol, etc.

Preferred solvent mixtures for the production of polyurethane polyureas and polyurethane-polyurea-polyhydrazodicarbonamides substituted by phosphonic ester groups are benzene/toluene, xylene/isopropanol (1:1:1:1), xylene/toluene/ tert.-butyl (1:1:1:); xylene/-toluene/ethyl glycol acetate/ isopropanol (1:1:1:1) and in particular, dimeric mixtures of toluene and isopropanol or toluene and tertiary butanol in a ratio of weight of 70 : 30 to 30 : 70. Strongly polar solvents such as dimethylformamide, dimethylacetamide, tetramethyl urea, etc. may also be used in suitable proportions. Where the process according to the invention is carried out in solution, it is preferred to work at temperatures in the range of from 10° to 45° C.

As already mentioned, it is possible by the process according to the invention to produce, inter alia, high molecular weight, linear polyurethane-polyureas and polyurethane-polyhydrazodicarbonamides with high solids contents (in solution form) and considerably improved fireproof properties. These compounds, which cannot be obtained by known processes, are characterized by the already defined urea group (=N—CO—N=) content and by an intrinsic viscosity (0.5% solution in dimethylformamide) of from 0.3 to 1.5.

It is surprising that, in the practical application of the process according to the invention, secondary reactions typical of ureas substituted by phosphonic acid ester radicals do not give rise to any crosslinking reactions during the polyaddition of bifunctional aminophosphonic acid esters and diisocyanates, because it is known from the literature (Chem. Ber. 102, 2143–2145, (1969)) that ureas of the constitution:

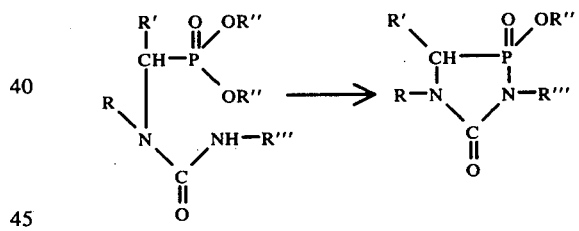

(R = butyl, R' = isopropyl, R'' = ethyl, R''' = phenyl radicals) cyclise very readily to form cyclic phosphohydantoin derivatives i.e. 1,4,2-diazaphospholidines, in accordance wih the above formula, accompanies by the elimination of alcohols. Where intramolecular ring closing reactions of this type do take place on the polymer chain formed, they do not result in cross-linking. Experience has shown that folding and clustering of the macromolecule may supress this ring formation through adverse steric conditions, so that inter-molecular condensations at elevated temperatures in the range of from 60° to 80° C would result in premature crosslinking. Secondary reactions of this type are, however, not observed in the practical application of the process according to the invention. By contrast, up to about 40 to 60% polyphosphohydantoin formation within the polymer chain may favorably be obtained in solvent-free end products (films) by heating to 140° to 150° C, as a result of which the heated films undergo an increase in hardness and a reduction in swellability which, however, is not due to an inter-molar crosslinking reaction.

One particular advantage of the process according to the invention is that long-chain, high molecular weight and, by virtue of their phosphorus content, highly flameproof polyaddition products, soluble in high concentration in the usual lacquer solvents, may also be obtained using sluggishly reacting aliphatic isocyanates. The polyaddition products obtainable in this way are further distinguished by outstanding gloss, fastness to light, high elasticity and other extremely good lacquer-grade properties. Flameproof polyaddition products obtained by the process according to the invention using aromatic diisocyanates are also eminently suitable for use as binders for physically drying lacquer systems, providing these lacquer systems are not required to be light-stable.

Particularly suitable lacquer binders are polyaddition products obtained by the process according to the invention using 1-isocyanato-3,3,5-trimethyl-5-isocyanatomethyl cyclohexane, 2,6-diisocyanato caproic acid esters or the vinyl telomers of these diisocyanates as the isocyanate component and diisocyanates containing phosphonic ester groups of constitution (A), hydroxyl polyesters and hydroxyl polycarbonates. Solutions of these polyaddition products, especially in the aforementioned mixtures of aromatic hydrocarbons and alcohols, are distinguished by their water-like clarity, by the absence of any tendency gel formation, by unlimited stability in storage and by outstanding film-forming properties. The film formation of lacquers produced with polyaddition products of this type as binders is based solely on physical drying through evaporation of the solvent. Lacquers containing polyaddition products of this type as binders are particularly suitable for quick-drying coatings of all types, especially for lacquering plastics and leather.

The polyaddition products obtainable by the process according to the invention are also thermoplastically processible plastics, and for this reason, may be converted by thermoplastic processing into shaped structures of any configuration.

If desired, the polyaddition products obtained by the process according to the invention may also be converted into crosslinked coatings, lacquers, duroplastic plastics, with the aid of 10 to 30% by weight of crosslinking reagents, such as triisocyanates, biuret, allophanate and isocyanurate polyisocyanates, epoxides, formaldehyde or formaldehyde donors.

The particular value of the process according to the invention for synthesizing a variety of different polyurethane polyureas, polyurethane-polyurea-polyhydrazodicarbonamide, polyurethane polyamides, etc., lies in the many different ways of controlling the solubility of the elastic and polypeptide-like, leather-like polyaddition products which may vary from elastic to hard in their property spectrum. The lateral phsophonic acid ester group act as spacer members. In this way, high concentrations of urea segments may be incorporated without any appreciable reduction of the solubility of the end product. If desired, the polyaddition products according to the invention may be synthesized, for example, by incorporating $\alpha,\omega$-dihydroxy polyethylene oxides with molecular weights in the range of from 1000 to 4000, in such a way that, despite their large content of phosphonic ester groups, they are even soluble in alcohol or alcohol-water mixtures.

The variability of the polyaddition products according to the invention in terms of solubility is attributable in particular to the combination of a number of commercially readily accessible aldehydes, diamines and dialkylphosphites, enabling a variety of different bifunctional aminophosphonic acid esters with shorter or longer radicals as spacer members to be synthesized and, in addition, varied through the constitution of the alkoxy radicals in the phosphonic acid esters. It is possible in this way to prepare solutions with extremely high solids contents, for example in the range of from 50 to 60% by weight, which although being produced with an $NCO:NH_2$-ratio of 1:1 do not exceed relatively low viscosities in the range of from 1000 to 40,000 cP at 20° C.

The wide range of variation of the invention illustrated by the following examples.

EXAMPLE 1

This Example demonstrates the production of relatively hard, polyamide-like diisocyanate polyaddition products with excellent film-forming properties whose solution level out surprisingly smoothly to leave films with a particularly pronounced gloss and excellent fireproof properties.

I. PREPARATION OF A RELATIVELY HIGH MOLECULAR WEIGHT DIISOCYANATE (= NCO-PREPOLYMER)

200 Parts by weight (0.1 mol) of an adipic acidethylene glycol polyester of OH-number 56 are dehydrated for 30 minutes at 120° C and then reacted for 30 minutes at that temperature with 44.4 parts by weight (0.2 mol) of 1-isocyanato-3,3,5-trimethyl-5-isocyanatomethyl cyclohexane (= isophorone diisocyanate), to form the $\alpha$, $\omega$-diisocyanato prepolymer. NCO-content: 3.4%.

II. PROCESS ACCORDING TO THE INVENTION

The $\alpha,\omega$-diisocyanate prepolymer prepared in accordance with I is dissolved in 510 parts by weight of toluene, and mixed at 30° C with 271 parts by weight of 61.8% toluene solution of the idealized diisocyanate (*)

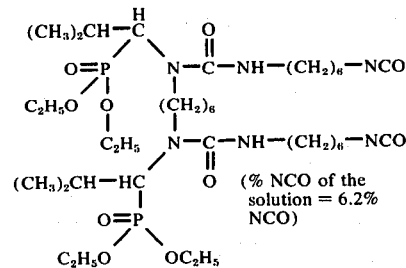

(% NCO of the solution = 6.2% NCO)

(*) The reaction of 1 mol of a diamine (A) with at least 2 mols of diisocyanate, $Q(NCO)_2$, generally gives a mixture consisting essentially of diisocyanate (B) to be used in accordance with the invention with excess diisocyanate, $Q(NCO)_2$, and oligomeric diisocyanates which are formed by a chainextending reaction between diamine (A) and diisocyanate $Q(NCO)_2$. Substantially pure diisocyanates (B) for use in accordance with the invention may be obtained by reacting diamines (A) with a large excess of diisocyanate $Q(NCO)_2$, and subsequently removing the excess diisocyanate, for example, by solvent extraction with hexane or cyclohexane. However, the diisocyanate (B) do not have to be prepared in pure form for the production of the end products according to the invention. This quantity contains 0.4 NCO equivalents (= 16.8 g of NCO). The chain-extending reaction is then carried out by the dropwise addition, over a period of 30 minutes, of a solution of 51 parts by weight of 1-amino-3,3,5-trimethyl-5-aminomethyl cyclohexane (= isophorone diamine) in 314 parts by weight of toluene and 928 parts by weight of isopropanol. An approximately 20% solution with a remarkably low viscosity of only 83 cP at 20° C is obtained. Despite this surprisingly low viscosity, films of high strength and polyamide-like feel may be produced from the solution. Sheets and films have remarkable gloss and go out immediately after they have been ignited. The solution may readily be adjusted to a solids content of approximately 55% by weight by distilling off solvent without gel formation occurring on cooling to room temperature. The films have a phosphorus content of about 2.68%. The urea group concentration amounts to about 12.6% by weight of unsubstituted urea equivalents.

When the procedure on which this Example is based is repeated except that α,ω-NCO prepolymers of polypropylene glycol (OH-number 56) α,ω-diaminopropylene glycol (molecular weight 2000) and hexane diol polycarbonate (OH-number 56) are used, high gloss films with a phosphorus content of about 2.6% are again obtained. All three of the films are self-extinguishing.

When 100 parts by weight of the high molecular weight polyurethane polyurea solutions (20% by weight) prepared in this Example are quickly stirred with 5 parts by weight of a biuret triisocyanate of 3 mols of hexamethylene diisocyanate and 1 mol of water or with 5 parts by weight of a biuret triisocyanate of 3 mols of 1-isocyanato-3,3,5-trimethyl-5-isocyanatomethyl cyclohexane and 1 ml of water, and the resulting two mixtures coated onto glass, sheet metal and wood substrates, hard, crosslinked, abrasion-resistant lacquer coatings of high light stability are obtained.

EXAMPLE 2

200 parts by weight (0.1 mol) of an adipic acidethylene glycol polyester of OH-number 56 are dehydrated for 20 minutes at 120° C, and subsequently reacted for 30 minutes at that temperature with 44.4 parts by weight of 1-isocyanato-3,3,5-trimethyl-5-isocyanatomethyl cyclohexane (0.2 mol) to form the α,ω-diisocyanato prepolymer. The temperature of the NCO-prepolymer is allowed to fall to 100° C, followed by dilution with 100 parts by weight of toluene. After cooling to 25° C, the solution of the NCO-prepolymer has added to it 510 parts by weight of toluene and 230 parts by weight of an 80% by weight toluene solution of the following idealized diisocyanate whose solution has an NCO-content of 7.3%:

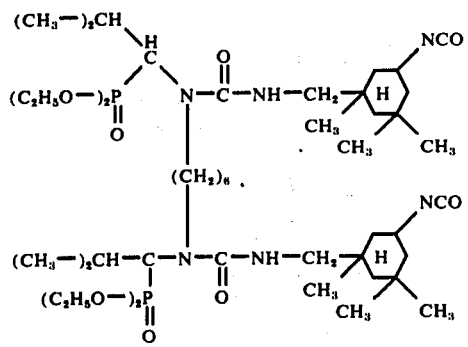

The chain-extending reaction is then carried out by the dropwise addition over a period of 30 minutes of solution of 51 parts by weight of 1-amino-3,3,5-trimethyl-5-aminomethyl cyclohexane (= isophorone diamine) in 403 parts by weight of toluene and 959 parts by weight of isopropanol. An approximately 20% solution with a remarkably low viscosity of only 116 cP at 20° C is obtained, although the polyaddition products contain approximately 12.1% by weight of unsubstituted area equivalents =N—CO—N= and although chain extension was carried out with an NCO:NH$_2$-ratio of 1. Conventional solutions of comparable urea group concentration, prepared with an NCO:NH$_2$— ratio of 1, are gels whose viscosity cannot be measured. The end products of the process according to the invention form high-gloss, flexible films which are substantially non-inflammable and self-extinguishing although they only have a phosphorus content of approximately 2.52%.

EXAMPLE 3

This example illustrates the use of two mixed chain extenders of different constitution, namely

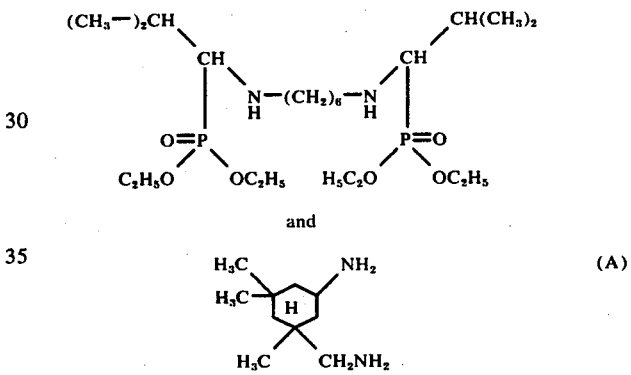

in a molar ratio of 1:1, chain extension of the NCO-prepolymer (0.1 mol) described in Example 1, in a mixture with 0.1 mol of 1-isocyanato-3,3,5-trimethyl-5-isocyanatomethyl cyclohexane (isophorone diisocyanate), with 0.1 mol of compound (B) and 0.1 mol of 1-amino-3,3,5-trimethyl-5-aminomethyl cyclohexane (isophorone diamine), being carried out in dimethylformamide (20% solution) in contrast to Example 1. Extremely low viscosity polyaddition products ($\eta = 35$ cP at 20° C) are obtained. Removal of the solvent by evaporation at 70° C leaves flexible, soft films. The end products contain about 6.9% by weight of unsubstituted urea equivalents. Average molecular weights as determined by osmometry are about 35,000. By virtue of the low viscosity of a 20% dimethylformamide solution, it is possible, despite the high molecular weight of the polyaddition products, to prepare even 60% solutions in dimethylformamide which do not gel at room temperature (= spacer effect of the phosphonic acid ester substituents). Despite the relatively low phosphorus content of films produced from these solutions (about 1.85% of phosphorus), the films are completely self-extinguishing. The ignition flames of a 2 cm wide, 20 cm long and 1 mm thick film ignited with a Bunsen flame show hardly any propagation, because the ignited edge of the film goes out immediately.

EXAMPLE 4

The procedure is exactly the same as in Example 3, using the following bifunctional aminophosphonic acid ester derivatives in a molar ratio of 1:1 with the following diamines and hydrazine hydrate.

The starting product for chain extension is the α,ω-diisocyanato prepolymer described in Example 1, I. Alcohol free solvents, preferably dimethylformamide, dimethylformamide/toluene, dimethylformamide/xylene, have to be used as solvents because the basicity of the aminophosphonic acid esters is extremely low, is further weakened by alchols due to associate formation and, hence, strong chain-terminating reactions take place with alcohols, for example, isopropanol, in for example, solvent mixtures of toluene and isopropanol (1:1).

0.1 mol of the α,ω-diisocyanato prepolymer described in Example 1, I and 0.1 mol of the 1-isocyanato-3,3,5-trimethyl-5-isocyanatomethyl cyclohexane are dissolved in 266.6 parts by weight of dimethylformamide, and chain extension carried out at room temperature with solutions in dimethylformamide of the following chain-extending agents, the quantity of dimethylformamide being such that approximately 50% solutions of polyurethane polyureas or polyurethane-polyurea polyhydrazodicarbonamides are formed which contain terminal phosphonic acid ester groups statistically distributed throughout the molecular structure.

a) 0.05 mol of [structure] + 0.05 mol of $H_2N-NH_2$ and 0.1 mol of [structure]

b) 0.1 mol of $H_2N-(CH_2)_6-NH_2$ and 0.1 mol of [structure]

c) 0.1 mol of [structure] and 0.1 mol of [structure]

d) 0.1 mol of [structure] and 0.1 mol of [structure]

e) 0.1 mol of [structure] and 0.1 mol of [structure]

f) 0.1 mol of [structure] and 0.1 mol of [structure]

Solutions of the polyaddition products in dimethylformamide are obtained after chain extension, being distinguished by remarkably low viscosities although they only have solids contents of 50% by weight and although chain extension was carried out with an $NCO:NH_2$-ratio of strictly 1.

| | | | |
|---|---|---|---|
| a) | 1200 cP/20° C | d) | 1120 cP/20° C |
| b) | 1400 cP/20° C | e) | 980 cP/20° C |
| c) | 1280 cP/20° C | f) | 1050 cP/20° C |

By coating solutions (a) to (f) onto glass, wood, metal or textile substrates at 20° C, it is possible to obtain clear, high-gloss flexible polyurethane coatings which are self-extinguishing after ignition of the films.

In the production of the polyurethane films described in this example, the dimethylformamide solvent may be replaced by solvent mixtures of toluene/isopropanol and xylene/isopropanol if all the bis-aminophosphonic acids of embodiments (a) to (f) (0.1 mol in each case)

are initially reacted with 0.2 mols of hexamethylene diisocyanate, tolylene diisocyanate, 1-isocyanato-3,3,5-trimethyl-5-isocyanatomethyl cyclohexane, tetramethylene diisocyanate, m-xylylene diisocyanate, to form the corresponding α,ω-diisocyanato prepolymers, these prepolymers then being added to prepolymer solution I of Example 1, in toluene or xylene, and chain extension subsequently being carried out with 1-amino-3,3,5-trimethyl-5-aminomethyl cyclohexane or 4,4'-diamino dicyclohexylmethane.

EXAMPLE 5

The procedure is exactly the same as in Example 4, using the following bifunctional aminophosphonic acid ester derivatives in a molar ratio of 1:1 with 1-amino-3,3,5-trimethyl-5-aminomethyl cyclohexane, 0.1 mol of 1-isocyanato-3,3,5-trimethyl-5-isocyanatomethyl cyclohexane (isophorone diisocyanate) being additionally added to the α,ω-diisocyanato prepolymer of Example 1, I and chain extension being carried out in dimethylformamide.

a) 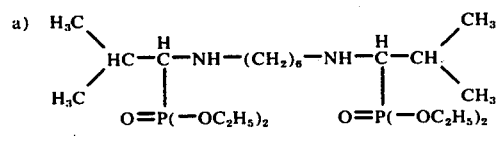

100 parts by weight of (0.2 mol)

b) 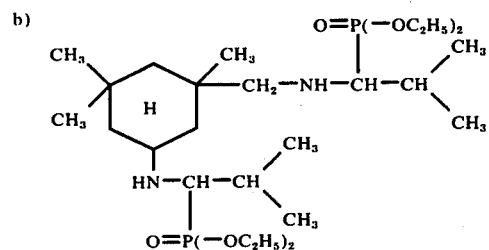

110.8 parts by weight (0.2 mol)

c) 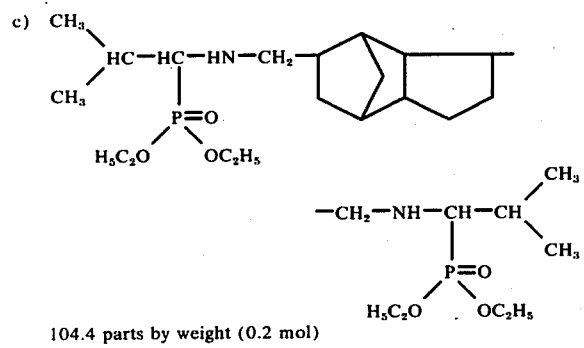

104.4 parts by weight (0.2 mol)

d) 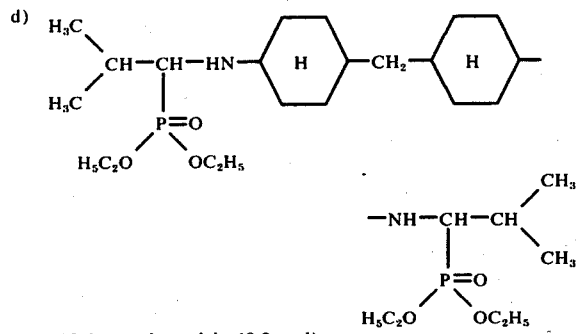

118.6 parts by weight (0.2 mol)

e) 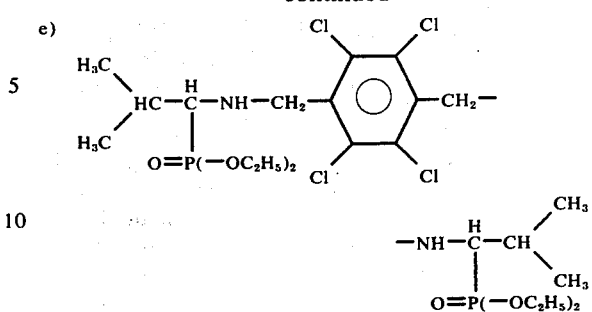

131.6 parts by weight (0.2 mol)

f) 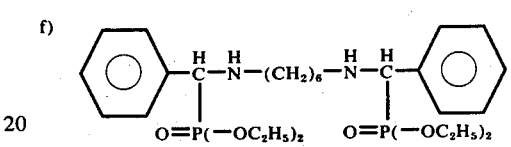

113.5 parts by weight (0.2 mol)

Relatively low-viscosity polyaddition products with the following viscosities are obtained in every case in the preparation of 50% solutions in dimethylformamide, based on comparable concentrations of conventional systems:

| a) | 2580 cP/20° C | d) | 4800 cP/20°C |
| b) | 3520 cP/20° C | e) | 3950 cP/20° C |
| c) | 4100 cP/20° C | f) | 2800 cP/20° C |

All the films produced from (a) to (f) are selfextinguishing when ignited with a Bunsen flame.

EXAMPLE 6

The chain extending procedure is exactly the same as in Example 2, using isophorone diamine as chain extender and prepolymers (0.1 mol) containing α,ω-NCO groups and having the following idealized constitutions, in each case together with 0.1 mol of hexamethylene diisocyanate:

a) 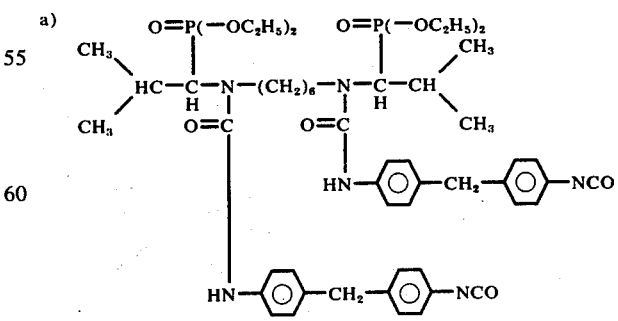

100 parts by weight (0.1 mol), 50% solution in toluene (% NCO: theoretical 4.2%, found 3.36% NCO)

b)
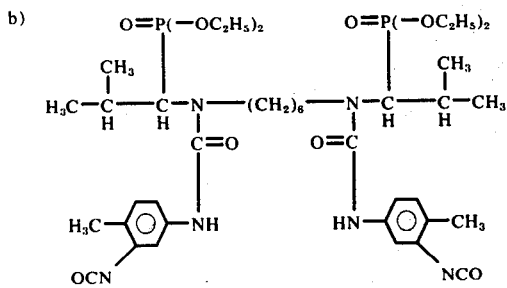

84.8 parts by weight (0.1 mol), 50% solution in toluene (% NCO = 4.9)

In both cases (a) and (b) solutions of relatively low viscosity are obtained, their viscosity values at 20° C being as follows:
a. 2350 cP
b. 3500 cP When flame-tested in accordance with Example 3, films (a) and (b) proved to be self-extinguishing.

EXAMPLE 7

This example demonstrates that polyureas which contain regularly recurring urea units substituted by phosphonic acid ester groups and which are soluble at room temperature in dimethylformamide as solvent may be obtained using the chain-extending agents according to the invention. By contrast, polyureas prepared from commercially interesting diisocyanates and the diamines on which they are based with an NCO:NH$_2$-ratio of 1 are either insoluble in dimethylformamide at room temperature or are only able to form at most 1 to 2% by weight solutions.

50 parts by weight (0.1 mol) of

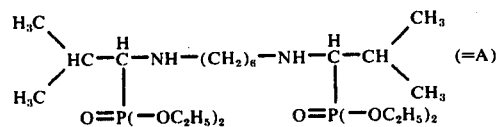

are dissolved in 145 parts by weight of dimethylformamide, followed by the dropwise addition, with stirring, of a solution of 22.2 parts by weight (0.1 mol) of 1-isocyanato-3,3,5-trimethyl-5-isocyanatomethyl cyclohexane in 145 parts by weight of dimethylformamide. A clear, approximately 20% polyurea solution containing approximately 69% by weight of compound (A) incorporated through substituted urea groups is obtained. Evaporation of the solution leaves glossy, hard polyurea films which are self-extinguishing and which have a phosphorus content of about 8.6%.

When compound (A) is replaced in this Example by corresponding phosphonic ester derivatives, namely by the
a. corresponding phosphonic acid methyl ester
b. corresponding phosphonic acid propyl ester
c. corresponding phosphonic acid-n-butyl ester
d. corresponding phosphonic acid cyclohexyl ester
e. corresponding phosphonic acid phenyl ester
clear, completely gel-free solutions are obtained from which it it possible to produce hard, glossy, self-extinguishing polyurea films.

EXAMPLE 8

Some exemplary embodiments of the production of bifunctional α-aminoalkane phosphonic acid dialkyl esters and their α,ω-diisocyanato urea derivatives (NCO-prepolymers) are described below in variants (a) to (f).

a. 232 g (2 mols) of hexamethylene diamine are introduced into a mixture of 288 g (4 mols) of isobutyraldehyde and 300 ml of methylene chloride. After 2 hours, the aqueous phase is separated off and all the readily volatile constituents distilled off under reduced pressure. Distillation of the residue (b.p.$_{0.1}$ : 95° to 104° C) leaves 432 g of the following bis-aldimine:

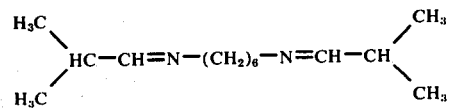

276 g (2 mol) of diethyl phosphite are added dropwise at 60° C to 224 g (1 mol) of bis-aldimine of isobutyraldehyde and hexamethylene diamine. The addition takes about 12 hours. The crude bis-(α-aminophosphonic acid ester) thus prepared:

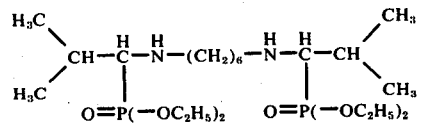

is added dropwise to a mixture of 336 g (2 mol) of hexamethylene diisocyanate in 520 g of toluene. After about 12 hours, the NCO-value of this approximately 62% solution remains constant (6.2% NCO).

b. This bis-(α-aminophosphonic acid diethyl ester) is prepared in the same way as described in (a) above. 250 g (0.5 mol) of this phosphonic acid derivative are added dropwise to a mixture of 222 g (1 mol) of 1-isocyanatomethyl-5-isocyanato-1,3,3-trimethyl cyclohexane in 124 g of toluene.

The NCO-content of this 80% solution falls to about 7% after 24 hours and then remains constant for several months.

c. 210 g (1 mol) of 4,4'-diaminodicyclohexylmethane are added dropwise to 288 g (4 mol) of isobutyraldehyde. The mixture is then boiled under reflux on a water separator until the calculated quantity of water has been separated off. All the low-boiling fractions are distilled off under reduced pressure. The crude bis-aldimine

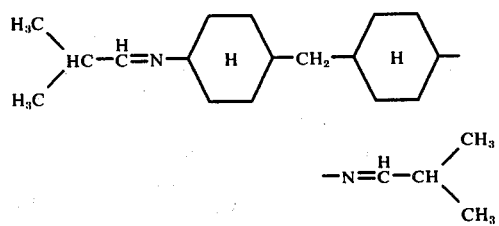

is added dropwise at a temperature of from 50° to 60° C to 276 g (2 mols) of diethylphosphite. The addition of phosphite to the CN-double bond is over after about 24 hours. The crude bis-(α-aminophosphonic acid diethyl ester)

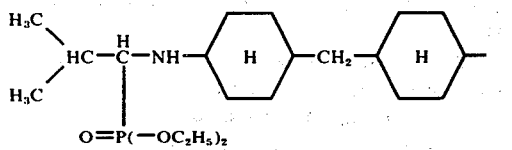

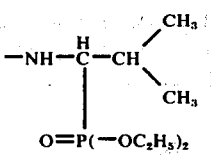

is added dropwise to a mixture of 336 g of hexamethylene diisocyanate in 240 g of toluene. The NCO-content of this 80% solution remains constant at about 7.1% aftersome 30 hours.

d. The bis-(α-aminophosphonic acid dialkyl ester) is prepared in the same way as described above in (c). The crude addition product is added dropwise at 40° to 50° C to a mixture of 444 g (2 mols) of 1-isocyanatomethyl-5-isocyanato-1,3,3-trimethyl cyclohexane in 452 g of toluene. The NCO-content of this 70% solution has fallen to 5.6% after 18 hours.

e. 170 g (1 mol) of 1-aminomethyl-5-amino-1,3,3-trimethyl cyclohexane are introduced into a mixture of 300 ml of methylene chloride and 144 g (2 mol) of isobutyraldehyde. After 3 hours, the aqueous phase is separated off and all the low-boiling fractions (maximum internal temperature 110° C) removed. The crude bis-aldimine

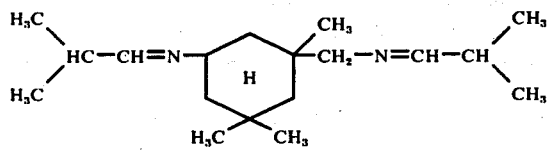

is then added dropwise at a temperature of from 60° to 70° C to 276 g (2 mols) of diethyl phosphite. Addition of the phosphite to the CN-double bond is over after 18 hours. The resulting crude bis-(α-aminophosphonic acid diethyl ester)

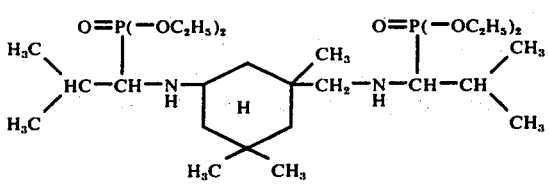

is added dropwise to a mixture of 336 g (2 mols) of hexamethylene diisocyanate in 380 g of toluene. The NCO-content remains constant at 6.5% after 24 hours.

f. The bis-(α-aminophosphonic acid diethyl ester) is prepared in the same way as described above in (c) and the crude aminophosphonic acid ester added dropwise to a mixture of 444 g (2 mols) of 1-isocyanatomethyl-5-isocyanato-1,3,3-trimethyl cyclohexane in 232 g of toluene. The 80% solution reaches its final constant NCO-value (approximately 7%) after some 32 hours.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Linear, film-forming diisocyanate polyaddition products soluble in lacquer solvents, wherein they contain from 10 to 69% by weight of structural units corresponding to the formula

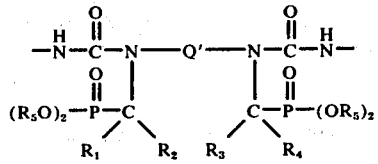

wherein
Q' represents a divalent $C_2$–$C_{18}$ alkyl radical, $C_4$–$C_{13}$ cycloalkyl radical, $C_7$–$C_{11}$ aralkyl radical or $C_6$–$C_{14}$ aryl radical optionally interrupted by oxygen, sulphur or nitrogen and optionally substituted by a $C_1$–$C_8$ alkyl radical, —$N(R_6)_2$, [$R_6$ = $C_1$–$C_8$ alkyl radical, $C_4$–$C_{10}$ cycloalkyl radical, $C_7$–$C_{11}$ aralkyl radical], $NO_2$- and/or halogen atoms,
$R_1$ and $R_2$ are the same or different and represent hydrogen, a $C_1$–$C_{18}$ alkyl radical, $C_4$–$C_{10}$ cycloalkyl radical or a $C_6$–$C_{10}$ aryl radical,
$R_3$ and $R_4$ are the same or different and represent hydrogen, a $C_1$–$C_{18}$ alkyl radical, $C_4$–$C_{10}$ cycloalkyl radical, $C_6$–$C_{10}$ aryl radical, in addition to which
$R_1$ and $R_2$ or $R_3$ and $R_4$ together with the carbon atom between nitrogen and phosphorus may form a 5- to 7-membered isocyclic ring, and
$R_5$ represents a $C_1$–$C_4$ alkyl, cyclohexyl or phenyl radical.

2. Diisocyanate polyaddition products as claimed in claim 1 wherein they contain from 10 to 69% by weight of structural units corresponding to the formula

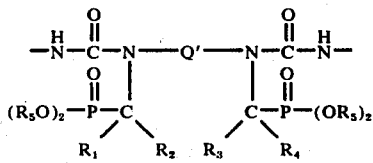

wherein
Q' represents a $C_2$–$C_8$ alkyl radical, $C_6$–$C_{13}$ cycloalkyl radical, $C_7$–$C_8$ aralkyl radical or $C_6$–$C_{14}$ aryl radical,
$R_1$, $R_2$, $R_3$ and $R_4$ are the same or different and represent hydrogen, a $C_1$–$C_4$ alkyl radical or $C_6$–$C_{10}$ aryl radical, in addition to which $R_1$ and $R_2$ or $R_3$ and $R_4$ together with the carbon atom between nitrogen and phosphorus may also form a 5- to 7-membered isocyclic ring and
$R_5$ represents a $C_1$–$C_4$ alkyl radical.

3. A process for the production of diisocyanate polyaddition products of the type claimed in claim 1 by reacting diisocyanates with relatively high molecular weight compounds containing two terminal hydroxyl groups and/or amino groups and having molecular weights in the range of from 400 to 8000 and optionally water and/or diols with a molecular weight below 400 and/or diamines with a molecular weight below 400 and/or hydrazines with a molecular weight below 400 as chain extenders, wherein diamines corresponding to the formula

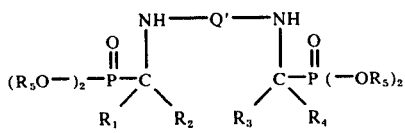

are used in the polyaddition reaction in such quantities that the addition products contain from 10 to 69% by weight of structural units corresponding to the formula

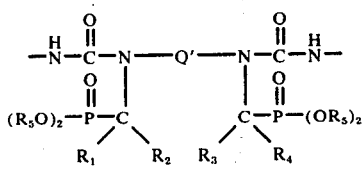

wherein $R_1$, $R_2$, $R_3$, $R_4$, $R_5$ and $Q'$ are as defined in claim 1.

4. A process for the production of polyaddition products of the type claimed in claim 2 by reacting diisocyanates with relatively high molecular weight compounds containing two terminal hydroxyl groups and/or amino groups and having molecular weights in the range of from 400 to 8000, and optionally water and/or diols with a molecular weight below 400 and/or diamines with a molecular weight below 400 and/or hydrazines with a molecular weight below 400 as chain-extending agents, wherein diamines corresponding to the formula

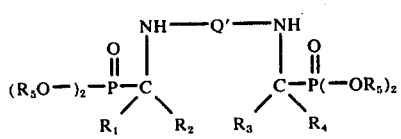

are used in the polyaddition reaction in such quantities that the addition products contain from 10 to 69% by weight of structural units corresponding to the formula

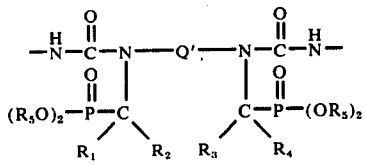

wherein $R_1$, $R_2$, $R_3$, $R_4$, $R_5$, and $Q'$ are as defined in claim 2.

5. A process for the production of polyaddition products of the type claimed in claim 1 by reacting diisocyanates with compounds containing two terminal hydroxyl groups and/or amino groups and having molecular weights in the range of from 400 to 8000 and optionally water and/or diols with a molecular weight below 400 and/or diamines with a molecular weight below 400 and/or hydrazines with a molecular weight below 400 as chain-extending agents, wherein compounds corresponding to the formula

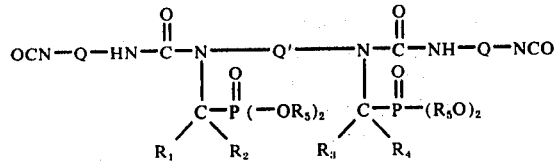

are used as diisocyanates in such quantities that the end products contain from 10 to 69% by weight of structural units of the formula

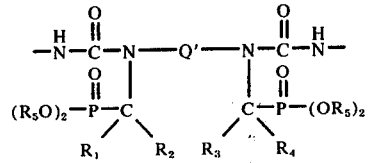

wherein $R_1$, $R_2$, $R_3$, $R_4$, $R_5$ and $Q'$ are as defined in claim 1, and Q represents a radical of the type obtained by removing the isocyanate groups from an organic diisocyanate with a molecular weight in the range of from 140 to 6000.

6. A process for the production of polyaddition products of the type claimed in claim 2 by reacting diisocyanates with compounds containing two terminal hydroxyl groups and/or amino groups and having molecular weights in the range of from 400 to 8000 and optionally, water and/or diols with a molecular weight below 400 and/or diamines with a molecular weight below 400 and/or hydrazines with a molecular weight below 400 as chain extending agents, wherein compounds corresponding to the formula

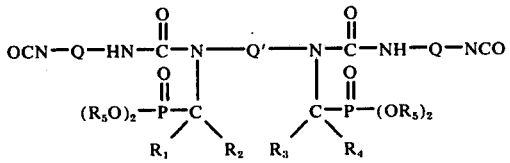

are used as dissocyanates in such quantities that the end products contain from 10 to 69% by weight of structural units corresponding to the formula

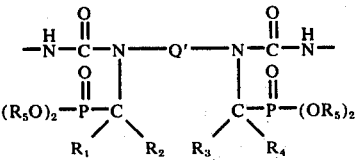

wherein $R_1$, $R_2$, $R_3$, $R_4$, $R_5$ and $Q'$ are as defined in claim 2 and Q represents a radical of the type obtained by removing the isocyanate groups from an organic diisocyanat with a molecular weight in the range of from 140 to 6000.

7. A process as claimed in claim 5 wherein both diisocyanates corresponding to the formula

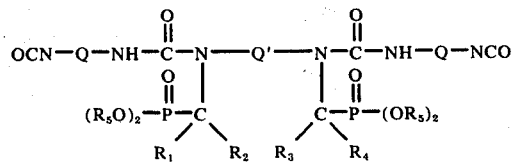

and diamines corresponding to the formula

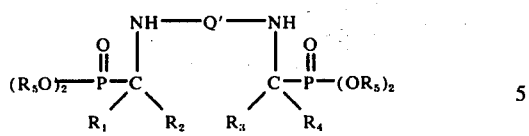

are together used in such quantities that the end products contain from 10 to 69% by weight of structural units corresponding to the formula

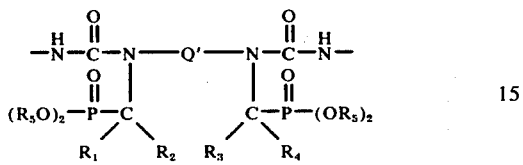

wherein $R_1$, $R_2$, $R_3$, $R_4$, $R_5$ and $Q'$ are as defined in claim 1 and Q represents a radical of the type obtained by removing the isocyanate groups from a diisocyanate with a molecular weight in the range of from 140 to 6000.

8. A process as claimed in claim 6, wherein both diisocyanates corresponding to the formula

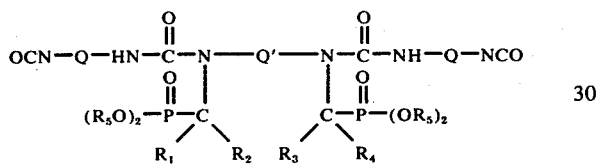

and also diamines corresponding to the formula

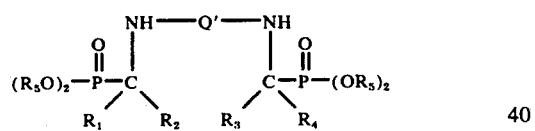

are together used in such quantities that the end products contain from 10 to 69% by weight of structural units corresponding to the formula

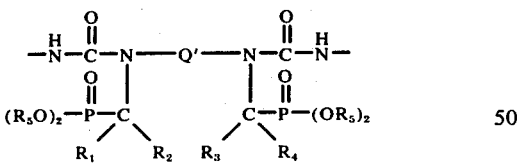

wherein $R_1$, $R_2$, $R_3$, $R_4$, $R_5$ and $Q'$ are as defined in claim 2 and Q represents a radical of the type obtained by removing the isocyanate groups from a diisocyanate with a molecular weight in the range of from 140 to 6000.

9. A process as claimed in claim 3 wherein the polyaddition products are produced in the presence of solvents.

10. The use of the polyaddition products claimed in claim 1 for producing surface coatings, lacquer coatings and impregnations.

11. A linear film forming polymer soluble in lacquer solvents selected from the group consisting of polyureas, polyhydrazocarbonamides, polyurethane polyureas, polyurethane polyhydrazocarbonamides, polyurea polyhydrazocarbonamides and polyurethane polyurea polyhydrazocarbonamide, wherein it contains from 10 to 69% by weight of structural units corresponding to the formula

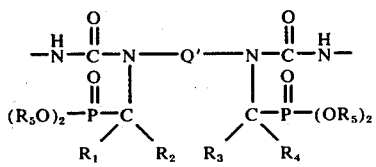

$Q'$ represents a divalent $C_2$–$C_{18}$ alkyl radical, $C_4$–$C_{13}$ cycloalkyl radical, $C_7$–$C_{11}$ aralkyl radical or $C_6$–$C_{14}$ aryl radical optionally interrupted by oxygen, sulphur or nitrogen and optionally substituted by a $C_1$–$C_8$ alkyl radical, —$N(R_6)_2$, [$R_6$ = $C_1$–$C_8$ alkyl radical, $C_4$–$C_{10}$ cycloalkyl radical, $C_7$–$C_{11}$ aralkyl radical], $NO_2$— and/or halogen atoms, $R_1$ and $R_2$ are the same or different and represent hydrogen or a $C_1$–$C_{18}$ alkyl radical, $C_4$–$C_{10}$ cycloalkyl radical or a $C_6$–$C_{10}$ aryl radical, $R_3$ and $R_4$ are the same or different and represent hydrogen, a $C_1$–$C_{18}$ alkyl radical, $C_4$–$C_{10}$ cycloalkyl radical, $C_6$–$C_{10}$ aryl radical, in addition to which $R_1$ and $R_2$ or $R_3$ and $R_4$ together with the carbon atom between nitrogen and phosphorus may form a 5- to 7-membered isocyclic ring, and $R_5$ represents a $C_1$–$C_4$ alkyl, cyclohexyl or phenyl radical.

12. The linear film forming polymer of claim 11 wherein $Q'$ represents the residue after the removal of the active hydrogens of hexamethylene diamine, 4,4'-diaminodicyclohexylmethane, 1-amino-3,5,5-trimethyl-5-aminomethyl cyclohexane, 4,4'-diamino diphenyl methane, 2,4-diamino toluene, or 2,6-diamino toluene.

$R_2$ and $R_3$ are the same or different and represent hydrogen or a methyl radical, $R_1$ and $R_4$ are the same or different and represent $C_1$–$C_3$ alkyl radical, benzyl radical, tolyl radical, provided that $R_1$ and $R_2$ or $R_3$ and $R_4$ together with the carbon atom between nitrogen and phosphorus may form a 5 membered isocyclic ring, and $R_5$ represents a $C_1$–$C_4$ alkyl radical.

13. The linear film forming polymer of claim 12 wherein $R_2$ and $R_3$ are hydrogen, $R_1$ and $R_4$ are isopropyl radicals and $R_5$ is an ethyl radical.

14. A process for the production of a linear film forming polymer soluble in lacquer solvents comprising reacting a. organic diisocyanates with b. compounds having a molecular weight of about 400 to 8000, and having two terminal groups selected from amino and hydroxyl and c. chain extenders with molecular weights below about 400 selected from the group consisting of water, diols, diamines and hydrazines, d. provided that sufficient diamine of the formula

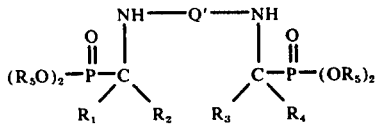

is used to give a polymer containing about 10 to 69% by weight of structural units corresponding to the formula

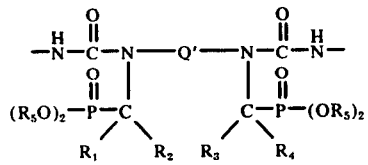

wherein $R_1$, $R_2$, $R_3$, $R_4$, $R_5$ and $Q'$ are as defined in claim 11.

15. The process of claim 14 wherein the organic diisocyante has a molecular weight of about 140 to 6000.

16. The process of claim 15 wherein the high molecular weight compounds having two terminal hydroxyl groups, are selected from the group consisting of dihydroxy polyesters, dihydroxy polyethers, dihydroxy polyacetals and dihydroxy polycarbonates and have molecular weights of about 800 to 2500.

17. The process of claim 16 wherein the organic diisocyanates are selected from the group consisting of hexamethylene diisocyanate, 1-isocyanato-3,3,5-trimethyl-5-isocyanatomethyl cyclohexane (≈isophorone diisocyanate), dicyclohexylmethane-4,4'-diisocyanate, m- and p-xylylene diisocyanate, 2,4-tolylene diisocyanate, 2,6-tolylene diisocyanate, 4,4'-diisocyanato-diphenylmethane, 1,5-naphthylene diisocyanate.

18. A process for the production of a linear film forming polymer soluble in lacquer solvents comprising reacting
a. organic diisocyanates with
b. compounds having molecular weight of about 400 to 8000 and having two terminal groups selected from amino and hydroxyl, and
c. chain extenders with molecular weights below about 400 selected from the group consisting of water, diols, diamines and hydrazines,
d. provided that sufficient diisocyanate of the formula

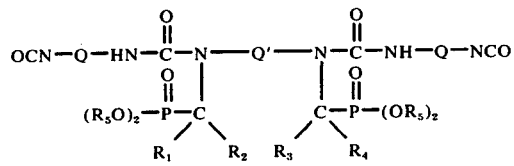

is used to give a polymer containing about 10 to 69 wt.% of structural units corresponding to the formula

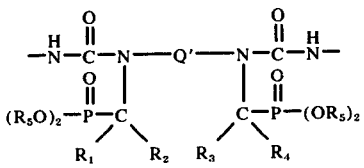

wherein $R_1$, $R_2$, $R_3$, $R_4$, $R_5$ and $Q'$ are as defined in claim 11 and Q represents a radical obtained by removing the isocyanate groups from an organic with a molecular weight of about 140 to 6000.

19. The process of claim 18 wherein diamines corresponding to the formula

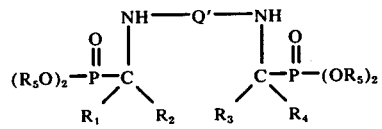

are used in addition to the diisocyanates in order to give the 10 to 69 wt.% of structural units and $R_1$, $R_2$, $R_3$, $R_4$, $R_5$ and $Q'$ are as defined in claim 11.

20. The process of claim 18 wherein
a. low molecular weight diisocyanates are reacted with high molecular weight dihydroxy compounds at an NCO:OH ratio of 1.5 to 2.3 to produce $\alpha,\omega$-NCO terminated prepolymers,
b. these prepolymers are mixed with the urea diisocyanates with phosphoric ester groups of formula (B), and
c. these high molecular weight mixtures are reacted with chain extenders selected from the group consisting of water, diols having molecular weights below about 400, diamines having molecular weights below about 400, hydrazines having a molecular weight below about 400 and the phosphonic ester containing diamines of formula (A) at a temperature of about $-50°$ to $140°$ C.

21. The process of claim 20 wherein the reaction is carried out at a temperature of about 5° to 40° C in an organic solvent.

22. The process of claim 20 wherein monomeric diisocyanate is also present in the mixture in about 1 to 6 fold molar quantity of the urea phosphoric ester containing diisocyanate of formula (B) and the molar ratio of the combination of NCO terminated prepolymer, monomeric diisocyanate and urea phosphoric ester containing diisocyanate to the chain extender is 1:1.

23. The process of claim 20 wherein the process is carried out in the absence of inert solvents.

* * * * *